(12) United States Patent
Miller

(10) Patent No.: US 7,070,620 B2
(45) Date of Patent: Jul. 4, 2006

(54) HOOK AND LOOP SYSTEM FOR ATTACHING A BREAST FORM PROSTHESES TO GARMENTS WITH BUILT-IN CUPS

(76) Inventor: Judith F. Miller, 78 Clark Hill Rd., East Hampton, CT (US) 06424

( * ) Notice: Subject to any disclaimer, the term of this patent is extended or adjusted under 35 U.S.C. 154(b) by 750 days.

(21) Appl. No.: 09/911,620

(22) Filed: Jul. 24, 2001

(65) Prior Publication Data

US 2002/0016632 A1  Feb. 7, 2002

Related U.S. Application Data

(63) Continuation of application No. 08/814,508, filed on Mar. 10, 1997, now abandoned.

(51) Int. Cl.
*A61F 2/24* (2006.01)

(52) U.S. Cl. .......................................................... 623/7

(58) Field of Classification Search ................... 623/7; 2/144, 267, 912, 913; 450/54, 55, 58
See application file for complete search history.

(56) References Cited

U.S. PATENT DOCUMENTS

| | | | | |
|---|---|---|---|---|
| 3,161,200 A | * | 12/1964 | Brickman | |
| 3,878,568 A | * | 4/1975 | Connelly | 623/7 |
| 4,681,587 A | * | 7/1987 | Eberl et al. | |
| 5,071,433 A | * | 12/1991 | Naestoft et al. | 623/7 |
| 5,480,429 A | * | 1/1996 | Weber-Unger | 623/7 |
| 5,895,423 A | * | 4/1999 | Becker et al. | 623/7 |
| 6,156,065 A | * | 12/2000 | Eaton | 623/7 |

* cited by examiner

*Primary Examiner*—Bruce Snow
(74) *Attorney, Agent, or Firm*—Alix, Yale & Ristas, LLP

(57) ABSTRACT

A breast form prosthesis has hook material attached to both front and back surfaces. A bust cup has loop material attached to the inside edges of the bust cup. A comfort pad is constructed of moisture absorbing material and is placed on the back of the prosthesis to absorb perspiration and reduce skin irritation.

18 Claims, 5 Drawing Sheets

HOOK AND LOOP SYSTEM FOR ATTACHING A BREAST FORM PROSTHESES TO GARMENTS WITH BUILT-IN CUPS

CROSS REFERENCE TO RELATED APPLICATION

This application is a continuation of U.S. application Ser. No. 08/814,508 filed Mar. 10, 1997 now abandoned.

BACKGROUND OF THE INVENTION

1. Field of the Invention

The invention relates in general to a breast prosthesis and in particular to a hook and loop system for attaching a breast form prosthesis to conventional bras and all other garments with built-in bust cups.

2. Prior Art

Methods presently available for wearing a breast form prosthesis are awkward and unnatural. The mastectomy bras available have pockets sewn in both cups thereby making the cup for the natural breast smaller, giving an uncomfortable fit due to the excess material. The excess material in mastectomy bras also makes the natural breast appear lumpy thereby making clothing such as jerseys, sweaters and dress blouses appear unsightly.

Another breast form prosthesis presently available adheres directly to the skin which causes skin irritation. It is difficult to measure and adhere it to the skin in the proper position and it detaches easily when perspiring under normal daily activities and activities such as swimming.

SUMMARY OF THE INVENTION

The above-discussed and other drawbacks and deficiencies of the prior art are overcome or alleviated by the hook and loop system for attaching a breast form prosthesis to garments with built-in bust cups of the present invention. A breast form prosthesis has hook material attached to both front and back surfaces. A bust cup has loop material attached to the inside edges of the bust cup. A comfort pad is constructed of moisture absorbing material and is placed on the back of the prosthesis to absorb perspiration and reduce skin irritation.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several figures.

DETAILED DESCRIPTION OF THE INVENTION

Figure 1:
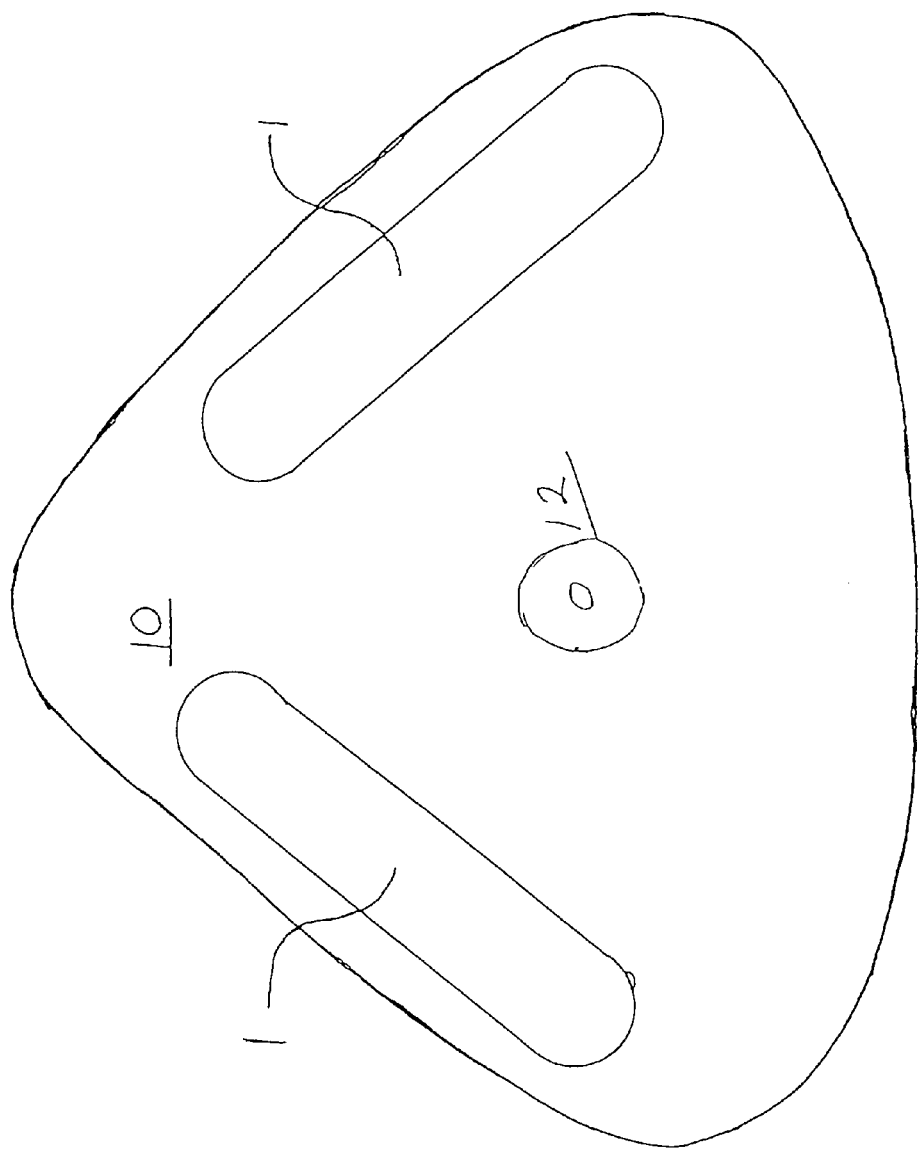
FIG. 1 is a front view of the prosthesis.
Figure 2:
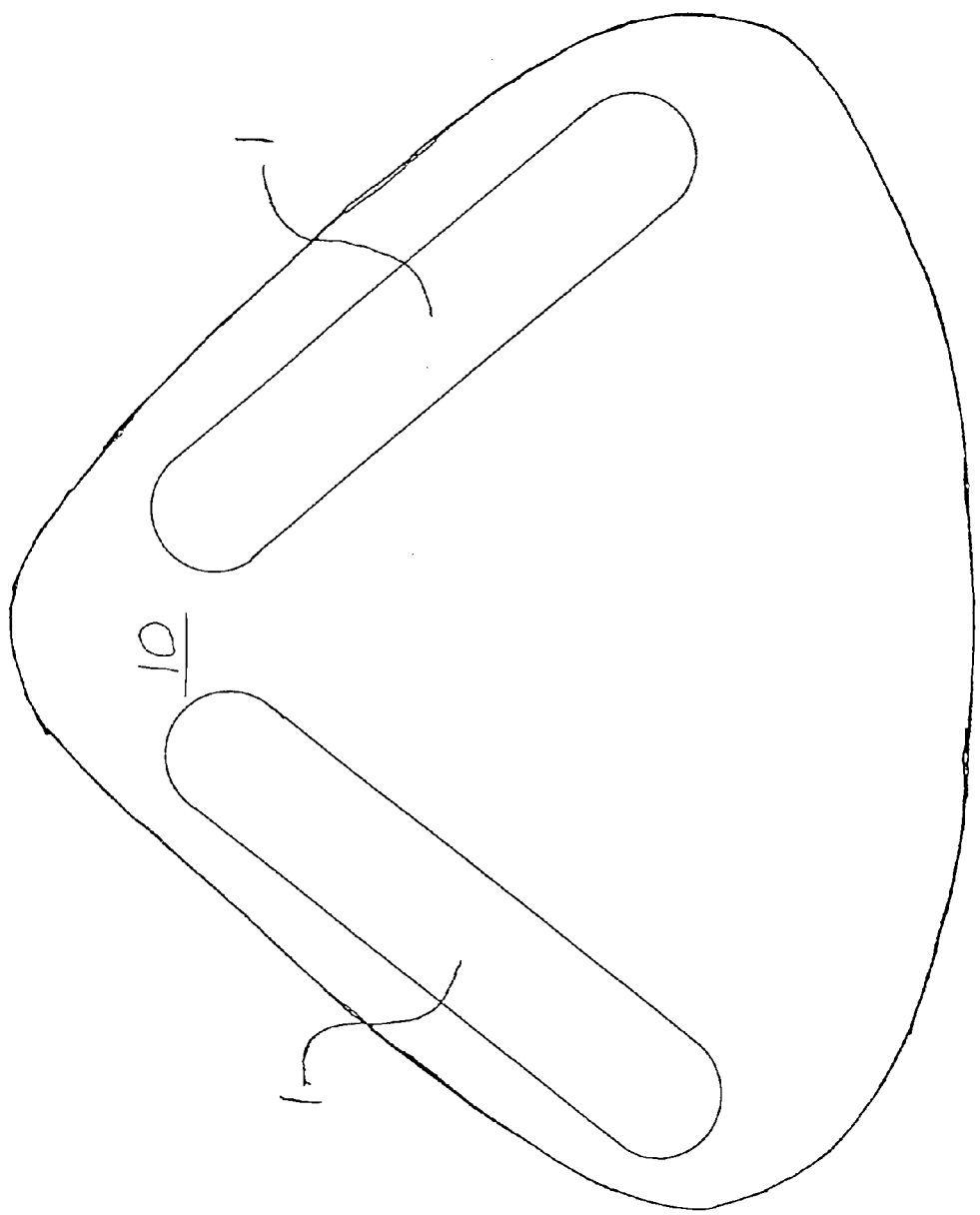
FIG. 2 is a rear view of the prosthesis.

FIG. 1 is a front view of the breast prosthesis 10 and is distinguished from the rear view shown in FIG. 2 by inclusion of a nipple area 12 typically found in a breast prosthesis. Hook material 1 is applied to the front surface of the breast prosthesis 10 near the edges of the prosthesis. As shown in FIG. 1, the hook material 1 is a strip having a length greater than its width and is positioned along the periphery of the prosthesis. FIG. 2 is a rear view of the prosthesis 10. As shown in FIG. 2, the back edges of prosthesis 10 include hook material 1. As shown in FIG. 2, the hook material 1 is a strip having a length greater than its width and is positioned along the periphery of the prosthesis.

Figure 3:
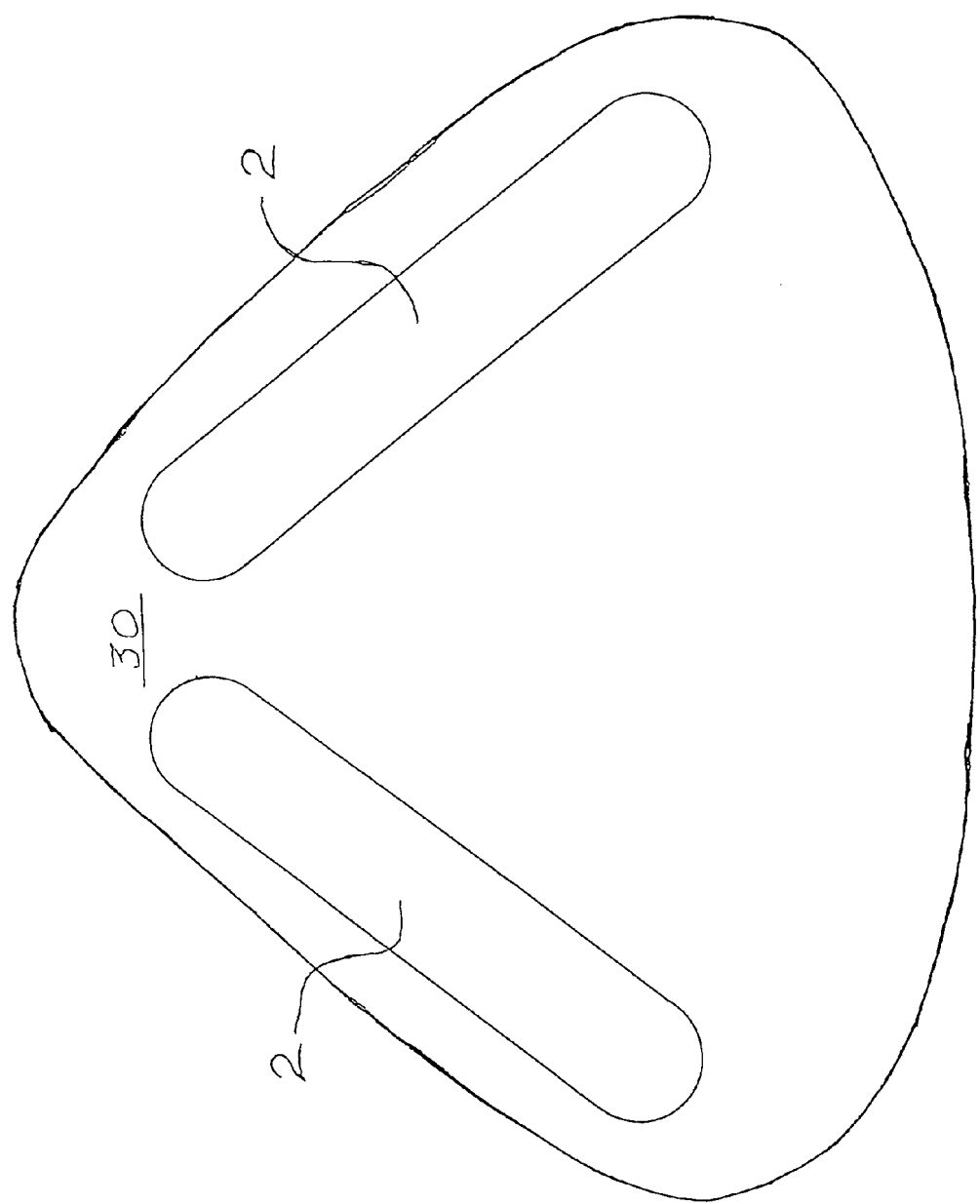
FIG. 3 is rear view of a bust cup.
Figure 4:
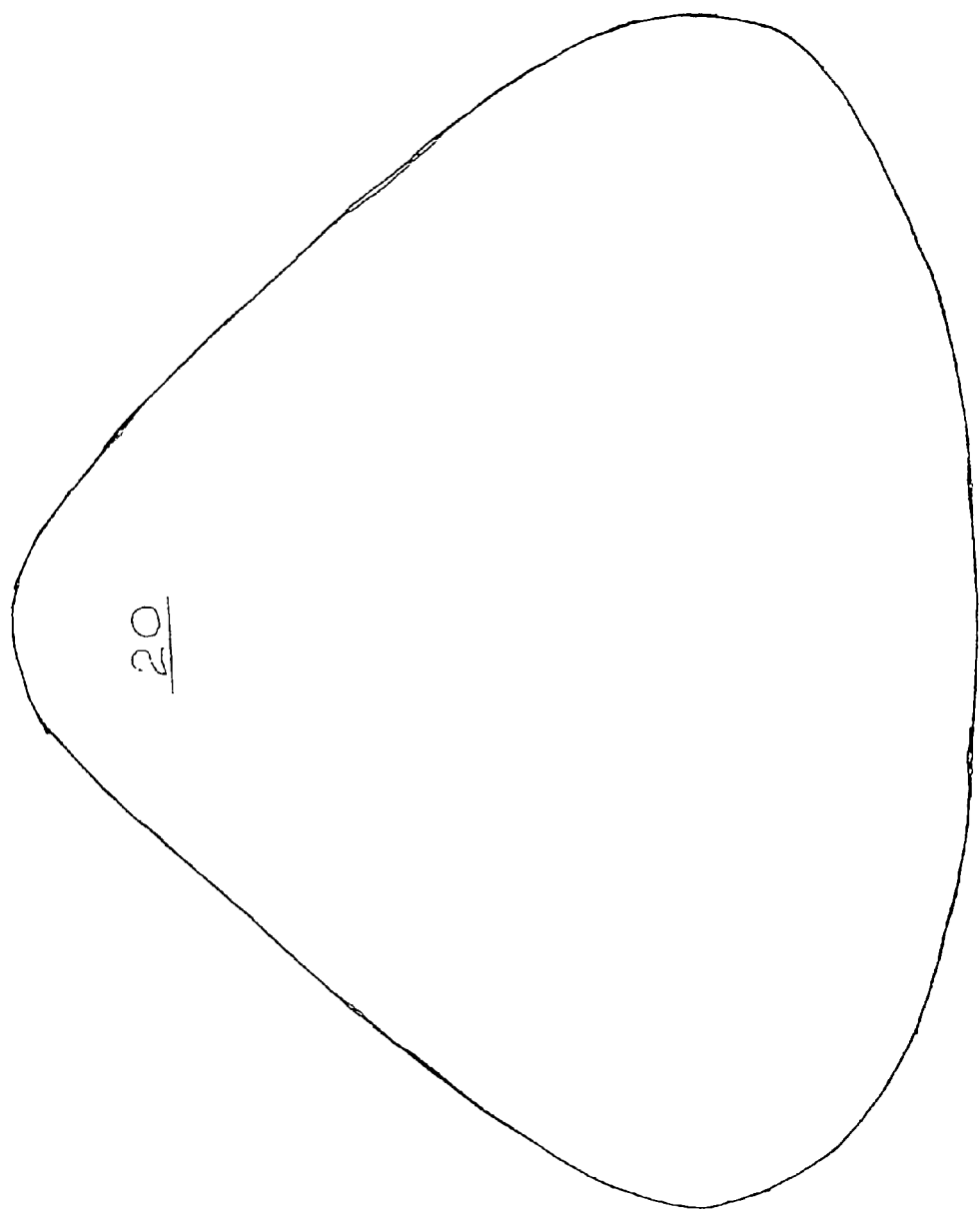
FIG. 4 is a front view of a comfort pad.

FIG. 3 is a rear view of a bust cup 30. Loop material 2 is attached (e.g., sewn) to the inside edges of bust cup 30 as shown in FIG. 3. Loop material 2 is provided in two strips each having a length greater than its width and positioned along the periphery of the bust cup 30. The loop material 2 on the inside of the bust cup 30 is positioned to engage the hook material 1 on the front surface of prosthesis 10. FIG. 4 is a front view of a comfort pad 20 which is placed against hook material 1 on back of prosthesis 10 (shown in FIG. 2). The comfort pad 20 provides a detachable backing for the prosthesis which is made of moisture absorbing material that can easily be removed and laundered.

Figure 5:
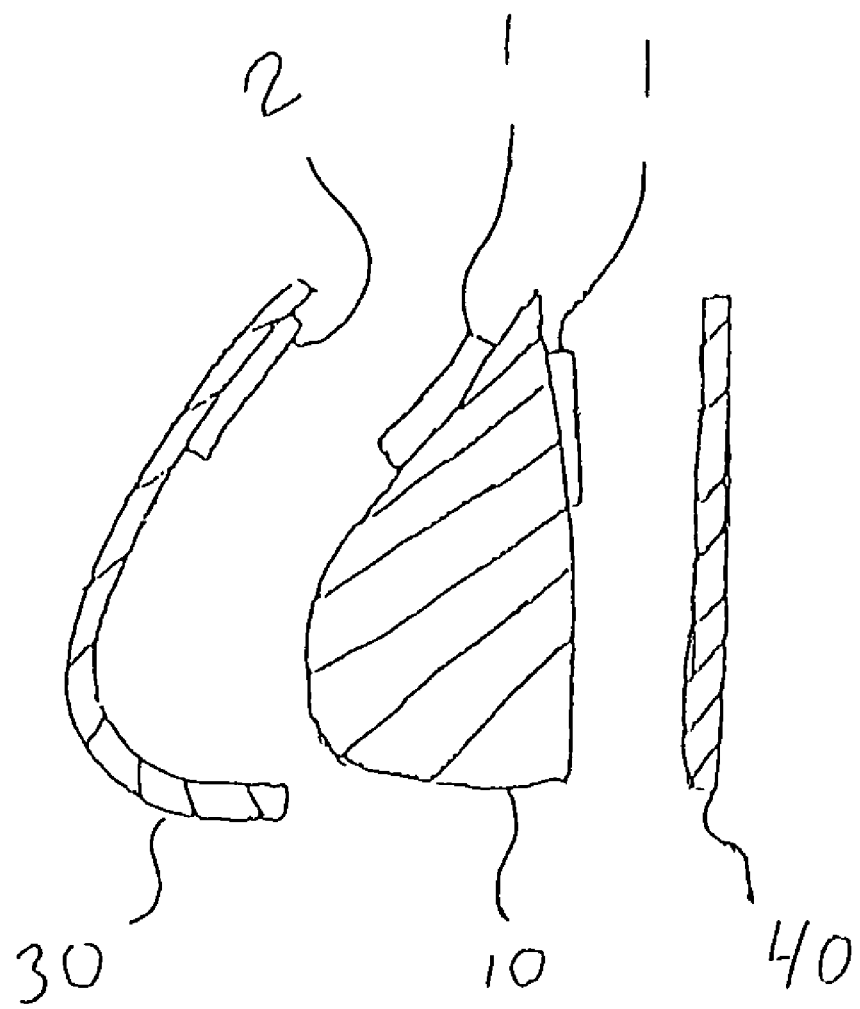
FIG. 5 is an exploded cross sectional view of the assembly of the present invention.

FIG. 5 is an exploded cross-sectional view of the assembly of the present invention. The prosthesis 10 is placed in bust cup 30 so that hook material 1 on the front of prosthesis 10 engages loop material 2 on the inside of bust cup 30. The comfort pad 40 is placed against the rear of prosthesis 10 and is secured to the prosthesis 10 through hook material 1 on the rear of prosthesis 10.

The present invention provides an improvement by which a mastectomy prosthesis can be worn in a conventional bra or garments with bust cups rather than mastectomy bras and other pocketed type garments thereby enabling the wearer to appear more natural and to feel more comfortable and secure.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A breast prosthesis and bust cup system adapted to be worn by a wearer comprising:
   a breast prosthesis having a front surface and a rear surface, said rear surface being positionable adjacent to a wearer's body;
   front hook material positioned on said front surface; rear hook material positioned on said rear surface;
   a bust cup including loop material engagable with said hook material, wherein said breast prosthesis is receivable in said bust cup; and
   a comfort pad attached to said rear surface through said rear hook material.

2. The breast prosthesis and bust cup system of claim 1 wherein said hook material comprises two strips of hook material positioned along a periphery of the breast prosthesis.

3. The breast prosthesis and bust cup system of claim 2 wherein each of said strips has a length greater than its width.

4. The breast prosthesis and bust cup system of claim 2 wherein said loop material comprises two strips of 100 p material positioned a long a periphery of the bust cup.

5. The breast prosthesis and bust cup system of claim 4 wherein each of said strips has a length greater than its width.

6. The breast prosthesis and bust cup system of claim 1 wherein said rear hook material comprises two strips of hook material positioned along a periphery of the breast prosthesis.

7. The breast prosthesis and bust cup system of claim 6 wherein each of said strips of rear hook material has a length greater than its width.

8. The breast prosthesis and bust cup system of claim 1, wherein said rear surface of said breast prosthesis has a substantially triangular shape with rounded corners.

9. The breast prosthesis and bust cup system of claim 8 wherein said hook and loop means comprise two strips of hook material positioned along a periphery of the breast prosthesis.

10. The breast prosthesis and bust cup system of claim 9 wherein each of said strips has a length greater than its width.

11. The breast prosthesis and bust cup system of claim 1, wherein said comfort pad has a substantially triangular shape with rounded corners.

12. A breast prosthesis adapted for use by a wearer comprising:
a front surface and a rear surface, said rear surface being positionable adjacent to a wearer's body;
hook material positioned on said front surface;
rear hook material positioned on said rear surface; and
a comfort pad removably attached to said rear surface through said rear hook material.

13. The breast prosthesis of claim 12 wherein said hook material comprises two strips of hook material positioned along a periphery of the breast prosthesis.

14. The breast prosthesis of claim 13 wherein each of said strips has a length greater than its width.

15. The breast prosthesis of claim 12 wherein said rear hook material comprises two strips of hook material positioned along a periphery of the breast prosthesis.

16. The breast prosthesis of claim 15 wherein each of said strips of rear hook material has a length greater than its width.

17. The breast prosthesis and bust cup system of claim 12, wherein said rear surface has a substantially triangular shape with rounded corners.

18. The breast prosthesis and bust cup system of claim 12, wherein said comfort pad has a substantially triangular shape with rounded corners.

* * * * *